(12) United States Patent
Hennemann et al.

(10) Patent No.: US 8,672,988 B2
(45) Date of Patent: Mar. 18, 2014

(54) METHOD AND DEVICE FOR LOCAL COOLING WITHIN AN ORGAN USING AN INTRAVASCULAR DEVICE

(75) Inventors: Willard W. Hennemann, Hudson (CA); Daniel Nahon, Ottawa (CA); Fredric Milder, Brookline, MA (US)

(73) Assignee: Medtronic CryoCath LP, Toronto, Ontario (CA)

(*) Notice: Subject to any disclaimer, the term of this patent is extended or adjusted under 35 U.S.C. 154(b) by 1353 days.

(21) Appl. No.: 11/257,331

(22) Filed: Oct. 24, 2005

(65) Prior Publication Data

US 2006/0089689 A1 Apr. 27, 2006

Related U.S. Application Data

(60) Provisional application No. 60/621,163, filed on Oct. 22, 2004.

(51) Int. Cl.
*A61F 7/12* (2006.01)
(52) U.S. Cl.
USPC .............................. 607/105; 607/104; 128/898
(58) Field of Classification Search
USPC ................................ 606/20–49; 607/104–105
See application file for complete search history.

(56) References Cited

U.S. PATENT DOCUMENTS

| | | | |
|---|---|---|---|
| 3,091,242 A | 5/1963 | Johnson, Jr. et al. |
| 3,170,465 A | 2/1965 | Henney et al. |
| 3,238,944 A | 3/1966 | Hirschhorn |
| 3,460,538 A | 8/1969 | Armstrong |
| 3,504,674 A | 4/1970 | Swenson et al. |
| 3,717,199 A | 2/1973 | Dienst |
| 3,736,936 A | 6/1973 | Basiulis et al. |
| 3,738,372 A | 6/1973 | Shioshvili |
| 3,768,484 A | 10/1973 | Gawura |
| 3,967,627 A | 7/1976 | Brown |
| 4,010,795 A | 3/1977 | Stenberg |
| 4,154,245 A | 5/1979 | Daily |
| 4,207,897 A | 6/1980 | Lloyd et al. |
| 4,259,961 A | 4/1981 | Hood, III |
| 4,416,281 A | 11/1983 | Cooper et al. |
| 4,605,006 A | 8/1986 | Jacques |
| 4,638,806 A | 1/1987 | Bartlett |
| 4,662,368 A | 5/1987 | Hussein et al. |
| 4,719,919 A | 1/1988 | Marchosky et al. |
| 4,947,843 A | 8/1990 | Wright et al. |
| 4,971,056 A | 11/1990 | Seacord |
| 5,014,695 A | 5/1991 | Benak et al. |

(Continued)

*Primary Examiner* — Aaron Roane
(74) *Attorney, Agent, or Firm* — Christopher & Weisberg, P.A.

(57) ABSTRACT

A method is disclosed for cooling a limited portion of a body organ by placing a cooling device into a blood vessel within a target organ; and activating the cooling device to cool tissue proximate the cooling device to a temperature below +34 degrees Centigrade. The blood vessel can be a vein or an artery and the cooling device can be a fixed diameter catheter or it can include a balloon. More particularly, the method of cooling can provide a method for treating injured ischemic and infarcted tissue by placing a device capable of passage through the vasculature into a target organ, wherein the device is capable of providing sufficient thermal exchange at a working region thereof to cool adjacent tissue; and activating the device to cool adjacent tissue to a temperature in the range of 0 degrees Centigrade to +36 degrees Centigrade. The method can further include placement of a second device capable of passage through the vasculature into the target organ, wherein the second device is capable of at least partially removing a blockage from a blood vessel.

6 Claims, 5 Drawing Sheets

(56) References Cited

U.S. PATENT DOCUMENTS

| | | |
|---|---|---|
| 5,057,117 A | 10/1991 | Atweh |
| 5,117,822 A | 6/1992 | Laghi |
| 5,150,706 A | 9/1992 | Cox et al. |
| 5,222,938 A | 6/1993 | Behl |
| 5,531,776 A | 7/1996 | Ward et al. |
| 5,549,559 A | 8/1996 | Eshel |
| 5,609,620 A | 3/1997 | Daily |
| 5,624,392 A | 4/1997 | Saab |
| 5,649,973 A | 7/1997 | Tierney et al. |
| 5,716,386 A | 2/1998 | Ward et al. |
| 5,800,486 A | 9/1998 | Thome et al. |
| 5,843,144 A | 12/1998 | Rudie et al. |
| 5,846,238 A | 12/1998 | Jackson et al. |
| 5,885,238 A * | 3/1999 | Stevens et al. ............... 604/6.14 |
| 5,931,860 A | 8/1999 | Reid et al. |
| 5,957,962 A | 9/1999 | Wallsten et al. |
| 5,957,963 A | 9/1999 | Dobak, III |
| 5,971,979 A * | 10/1999 | Joye et al. ...................... 606/21 |
| 6,009,351 A | 12/1999 | Flachman |
| 6,019,783 A | 2/2000 | Philips et al. |
| 6,042,559 A | 3/2000 | Dobak, III |
| 6,051,019 A | 4/2000 | Dobak, III |
| 6,064,914 A | 5/2000 | Trachtenberg |
| 6,090,132 A | 7/2000 | Fox |
| 6,096,068 A | 8/2000 | Dobak, III et al. |
| 6,126,684 A | 10/2000 | Gobin et al. |
| 6,139,569 A | 10/2000 | Ingle et al. |
| 6,146,411 A | 11/2000 | Noda et al. |
| 6,149,677 A | 11/2000 | Dobak, III |
| 6,156,057 A | 12/2000 | Fox |
| 6,176,857 B1 | 1/2001 | Ashley |
| 6,188,930 B1 | 2/2001 | Carson |
| 6,224,624 B1 | 5/2001 | Lasheras et al. |
| 6,231,595 B1 | 5/2001 | Dobak, III |
| 6,235,048 B1 | 5/2001 | Dobak, III |
| 6,238,428 B1 | 5/2001 | Werneth et al. |
| 6,248,126 B1 | 6/2001 | Lesser et al. |
| 6,251,130 B1 | 6/2001 | Dobak, III et al. |
| 6,254,626 B1 | 7/2001 | Dobak, III et al. |
| 6,261,312 B1 | 7/2001 | Dobak, III et al. |
| 6,312,452 B1 | 11/2001 | Dobak, III et al. |
| 6,325,818 B1 | 12/2001 | Werneth |
| 6,350,262 B1 | 2/2002 | Ashley |
| 6,358,273 B1 | 3/2002 | Strul et al. |
| 6,364,899 B1 | 4/2002 | Dobak, III |
| 6,445,957 B1 | 9/2002 | Bolmsjo |
| 6,451,045 B1 | 9/2002 | Walker et al. |
| 6,458,150 B1 * | 10/2002 | Evans et al. .................. 607/105 |
| 6,464,716 B1 | 10/2002 | Dobak, III et al. |
| 6,471,717 B1 | 10/2002 | Dobak, III et al. |
| 6,475,231 B2 | 11/2002 | Dobak, III et al. |
| 6,478,812 B2 | 11/2002 | Dobak, III et al. |
| 6,482,226 B1 | 11/2002 | Dobak, III |
| 6,491,716 B2 | 12/2002 | Dobak III et al. |
| 6,497,721 B2 | 12/2002 | Ginsburg et al. |
| 6,520,933 B1 | 2/2003 | Evans et al. |
| 6,533,804 B2 | 3/2003 | Dobak, III et al. |
| 6,540,771 B2 | 4/2003 | Dobak, III et al. |
| 6,544,264 B2 | 4/2003 | Levine et al. |
| 6,551,349 B2 | 4/2003 | Lasheras et al. |
| 6,558,412 B2 | 5/2003 | Dobak, III |
| 6,576,000 B2 | 6/2003 | Carrison |
| 6,576,002 B2 | 6/2003 | Dobak, III |
| 6,582,455 B1 | 6/2003 | Dobak, III et al. |
| 6,585,689 B1 | 7/2003 | Macoviak et al. |
| 6,589,271 B1 | 7/2003 | Tzeng et al. |
| 6,605,106 B2 | 8/2003 | Schwartz |
| 6,607,517 B1 | 8/2003 | Dae et al. |
| 6,610,083 B2 | 8/2003 | Keller et al. |
| 6,620,188 B1 | 9/2003 | Ginsburg et al. |
| 6,623,514 B1 | 9/2003 | Chin |
| 6,623,516 B2 | 9/2003 | Saab |
| 6,641,602 B2 | 11/2003 | Balding |
| 6,641,603 B2 | 11/2003 | Walker et al. |
| 6,648,880 B2 | 11/2003 | Chauvet et al. |
| 6,648,906 B2 | 11/2003 | Lasheras et al. |
| 6,648,907 B2 | 11/2003 | Larnard et al. |
| 6,648,908 B2 | 11/2003 | Dobak, III et al. |
| 6,652,566 B2 | 11/2003 | Larnard et al. |
| 6,660,026 B2 | 12/2003 | Larnard et al. |
| 6,676,689 B2 | 1/2004 | Dobak, III et al. |
| 6,676,690 B2 | 1/2004 | Werneth |
| 6,679,907 B2 | 1/2004 | Dobak, III et al. |
| 6,682,551 B1 | 1/2004 | Worthen et al. |
| 6,685,733 B1 | 2/2004 | Dae et al. |
| 6,692,519 B1 | 2/2004 | Hayes, Jr. |
| 6,695,873 B2 | 2/2004 | Dobak, III et al. |
| 6,699,269 B2 | 3/2004 | Khanna |
| 6,702,783 B1 | 3/2004 | Dae et al. |
| 6,702,840 B2 | 3/2004 | Keller et al. |
| 6,702,842 B2 | 3/2004 | Dobak, III et al. |
| 6,716,236 B1 | 4/2004 | Tzeng et al. |
| 6,719,723 B2 | 4/2004 | Werneth |
| 6,726,708 B2 | 4/2004 | Lasheras et al. |
| 6,726,709 B1 | 4/2004 | Lennox |
| 6,733,518 B2 | 5/2004 | Larnard |
| 6,736,837 B2 | 5/2004 | Fox |
| 6,740,109 B2 | 5/2004 | Dobak, III |
| 6,743,200 B2 | 6/2004 | Larnard et al. |
| 6,746,464 B1 * | 6/2004 | Makower ...................... 606/185 |
| 6,746,474 B2 | 6/2004 | Saadat |
| 6,749,585 B2 * | 6/2004 | Aliberto et al. ............... 604/113 |
| 6,752,786 B2 | 6/2004 | Callister |
| 6,755,850 B2 | 6/2004 | Dobak, III |
| 6,755,851 B2 | 6/2004 | Noda et al. |
| 2001/0032004 A1 * | 10/2001 | Werneth ........................ 607/105 |
| 2002/0004675 A1 | 1/2002 | Lasheras |
| 2002/0032430 A1 * | 3/2002 | Luo et al. ...................... 604/512 |
| 2002/0049484 A1 | 4/2002 | Werneth et al. |
| 2002/0068964 A1 | 6/2002 | Dobak, III |
| 2002/0077682 A1 | 6/2002 | Lee et al. |
| 2002/0091429 A1 | 7/2002 | Dobak, III et al. |
| 2002/0091430 A1 | 7/2002 | Dobak, III et al. |
| 2002/0095200 A1 | 7/2002 | Dobak, III et al. |
| 2002/0103519 A1 | 8/2002 | Dobak, III et al. |
| 2002/0116039 A1 | 8/2002 | Walker et al. |
| 2002/0128638 A1 * | 9/2002 | Chauvet et al. ................. 606/21 |
| 2002/0151942 A1 | 10/2002 | Walker et al. |
| 2002/0151944 A1 | 10/2002 | Walker et al. |
| 2002/0151945 A1 | 10/2002 | Gobin et al. |
| 2002/0151946 A1 | 10/2002 | Dobak, III |
| 2002/0161351 A1 | 10/2002 | Samson et al. |
| 2002/0169490 A1 | 11/2002 | Noda et al. |
| 2002/0193854 A1 | 12/2002 | Dobak, III et al. |
| 2002/0193855 A1 | 12/2002 | Dobak, III |
| 2002/0198579 A1 | 12/2002 | Khanna |
| 2003/0009206 A1 | 1/2003 | Dobak, III et al. |
| 2003/0014097 A1 | 1/2003 | Putz et al. |
| 2003/0028230 A1 | 2/2003 | Dobak, III et al. |
| 2003/0040782 A1 | 2/2003 | Walker et al. |
| 2003/0060864 A1 | 3/2003 | Whitebook et al. |
| 2003/0088299 A1 | 5/2003 | Magers et al. |
| 2003/0135252 A1 | 7/2003 | MacHold et al. |
| 2003/0139791 A1 | 7/2003 | Dobak, III |
| 2003/0144714 A1 | 7/2003 | Dobak, III |
| 2003/0195597 A1 | 10/2003 | Keller et al. |
| 2003/0225442 A1 | 12/2003 | Saadat |
| 2004/0044388 A1 | 3/2004 | Pham et al. |
| 2004/0068311 A1 | 4/2004 | Dobak, III et al. |
| 2004/0102826 A1 | 5/2004 | Lasheras et al. |
| 2004/0102827 A1 | 5/2004 | Werneth |
| 2004/0106969 A1 | 6/2004 | Dobak, III et al. |
| 2004/0116988 A1 | 6/2004 | Hammack et al. |

* cited by examiner

METHOD AND DEVICE FOR LOCAL COOLING WITHIN AN ORGAN USING AN INTRAVASCULAR DEVICE

CROSS-REFERENCE TO RELATED APPLICATION

This application is related to and claims priority to U.S. Provisional Patent Application Ser. No. 60/621,163, filed Oct. 22, 2004 entitled TREATING A CARDIAC INFARCT, the entirety of which is incorporated herein by reference.

STATEMENT REGARDING FEDERALLY SPONSORED RESEARCH OR DEVELOPMENT n/a

FIELD OF THE INVENTION

The present invention relates to medical methods and equipment, and more particularly to a method and apparatus for local cooling within an organ using an intravascular device.

BACKGROUND OF THE INVENTION

It is well known that reduction of tissue temperature can greatly retard or suspend tissue necrosis. Recently, considerable attention has been given to apparatus and methods of cooling body organs to protect them from the consequences of disease and accidental trauma, as well as during the trauma of emergency and elective surgery.

One approach to organ cooling is to lower the temperature of the entire body, and thus all of its organs with it. This approach requires a gradual, extended cooling period to be accomplished safely, and still produces undesirable side effects. Because the body naturally fights to preserve heat in the vial organs, it can take hours to cool the body's organs.

Somewhat more focused techniques and apparatus for organ cooling have been developed that provide for cooling the blood supply to the target organ by placing a cooling structure within a blood vessel that supplies the entire target organ or a substantial portion thereof. However, cooling an organ by cooling its blood supply requires considerable cooling power; high turbulence around the cooling transfer region to promote heat transfer across the cooling tip area, and it can still take a considerable amount of time to cool the target organ and the cooled blood can precipitate undesirable side effects, such as shivering and patient discomfort.

An alternative to indirectly cooling an organ by cooling the entire body or the blood that supplies an organ is to directly cool the target tissue within an organ. For example, myocardial tissue is routinely preserved in a healthy state in the absence of an oxygen rich blood supply during "open heart" procedures by interrupting blood flow to the heart and packing it with ice or placing it into an ice-filled basin. Although an ice bath plunge can provide immediate effective results for limiting tissue damage, it is clearly an "invasive" procedure, as are some other techniques that provide for surface application or envelopment of an organ with a cooling apparatus.

In view of the above limitations, it would be desirable to minimize tissue necrosis as quickly and completely as possible using a minimally invasive technique.

SUMMARY OF THE INVENTION

The present invention provides apparatus and a method for rapidly cooling organ tissue using a minimally invasive technique. More particularly, the invention provides a device, such as a catheter, that is capable of passage through the vasculature into a target organ, rather than merely in the vasculature that leads to the target organ, wherein the device provides sufficient thermal exchange at a working region thereof to cool adjacent tissue within the organ to a point between normal body temperature and slightly above the freezing point for the cells of the tissue within a few seconds.

In an exemplary method in accordance with the invention, a limited portion of a body organ is cooled by placing a cooling device into a blood vessel within a target organ; and activating the cooling device to cool tissue proximate the cooling device to a temperature below +36 degrees Centigrade. The blood vessel can be a vein or an artery and the cooling device can be a fixed diameter catheter or it can include a balloon.

More particularly, the method of cooling can provide a method for treating injured ischemic and infarcted tissue by placing a device capable of passage through the vasculature into a target organ, wherein the device is capable of providing sufficient thermal exchange at a working region thereof to cool adjacent tissue; and activating the device to cool adjacent tissue to a temperature in the range of 0 degrees Centigrade to +36 degrees Centigrade.

The method can further include placement of a second device capable of passage through the vasculature into the target organ, wherein the second device is capable of at least partially removing a blockage from a blood vessel.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein like designations refer to like elements, and wherein.

DETAILED DESCRIPTION OF THE INVENTION

Figure 1:
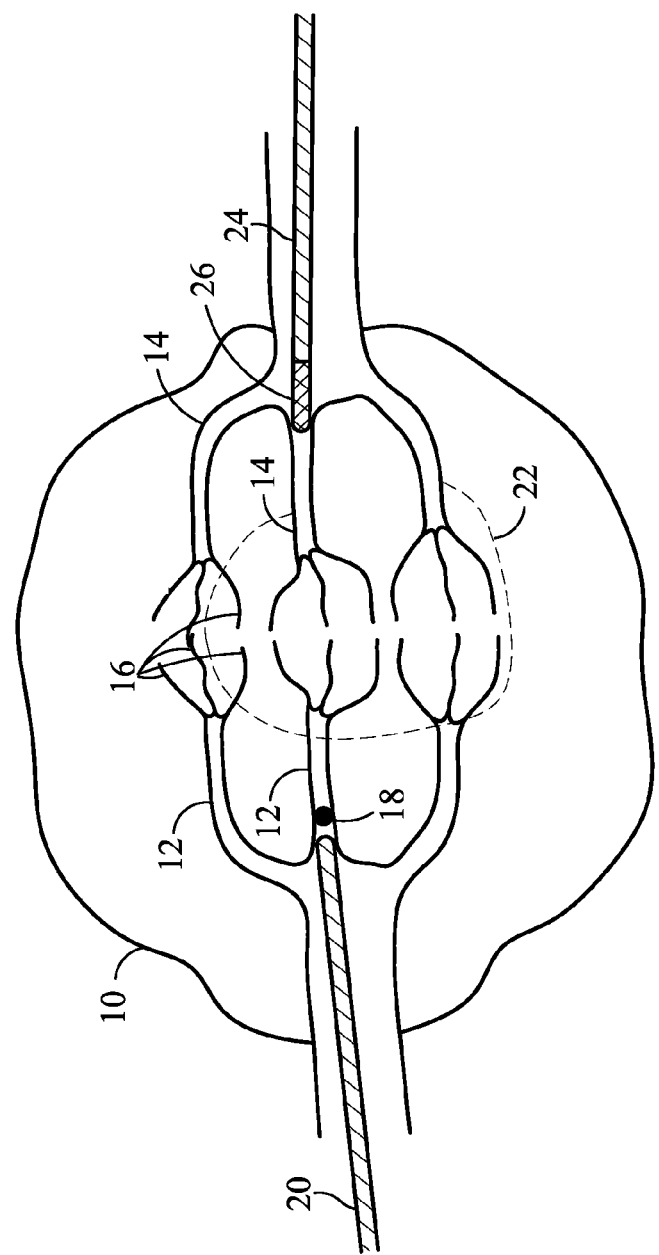
FIG. 1 is an illustration of a portion of organ tissue being treated in accordance with a method in accordance with the invention.

The present invention provides localized cooling within the vasculature of an organ to very quickly chill a precise location proximate the intravascular device. FIG. 1 is a stylized representation of an interior portion of an organ 10, such as a kidney, the brain, or the heart having a network of blood vessels including arteries 12, that supply the organ with oxygenated blood, and veins 14 that conduct oxygen depleted blood away from the organ. Very small blood vessels known as capillaries 16 provide a path for blood to move from the arteries 12 to the veins 14 and for oxygen to be exchanged between the capillaries and the surrounding tissue.

Continuing to refer to FIG. 1, an arterial blockage 18, such as a blood clot, is shown in an artery 12. Because of the blockage, tissue beyond the blockage is deprived of blood.

This is known as an "infarct" or "infarction" and it leads to necrosis resulting from obstruction of the blood supply to living tissue. Less than a complete blockage or flow insufficiency to part of the organ tissue is known as ischemia. Either condition is serious and requires some form of treatment, such as drug therapy or surgical intervention, to preserve life and to limit tissue damage. Because damage to organ tissue can be substantially irreversible, prompt detection and treatment of these conditions is highly desirable.

Using a device 20 known in the art, the blockage 18 is can be approached from the arterial side of the blockage and known techniques are used to dissolve or remove the blockage. However, as described above, a region of tissue 22 downstream of the blockage is deprived of oxygenated blood. Thus, in accordance with the present invention, a cooling device, such as a catheter 24 described in greater detail below, is advanced through a vein 14 on the venous side of the blockage 18 to the region of tissue 22 proximate the blockage. A working portion of the catheter, such as a distal end region 26, is cooled to a temperature as desired between −10 C to +30 C. By cooling the region of tissue 22, its need for oxygen is decreased, thereby extending the period of time for removal of the blockage 18. In addition, preclinical data suggests that tissue cooling reduces reperfusion injury after blood flow to the ischemia or infarct zone is restored.

It will be appreciated by one skilled in the art that the above method can also be performed by placing the cooling catheter 24 on the arterial side proximal to the blockage. In this configuration, the cooling catheter 24 may be combined with a catheter used to remove the blockage. Alternatively, the cooling catheter 24 and the catheter used to remove the blockage may be separate devices.

Figure 2:
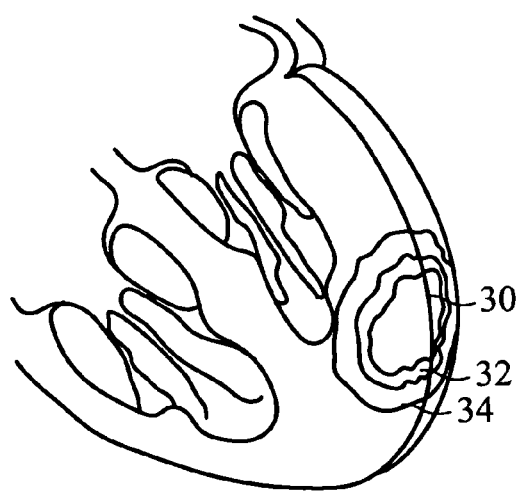
FIG. 2 is an cross-sectional illustration of a portion of a heart having a myocardial infarction.
Figure 3:
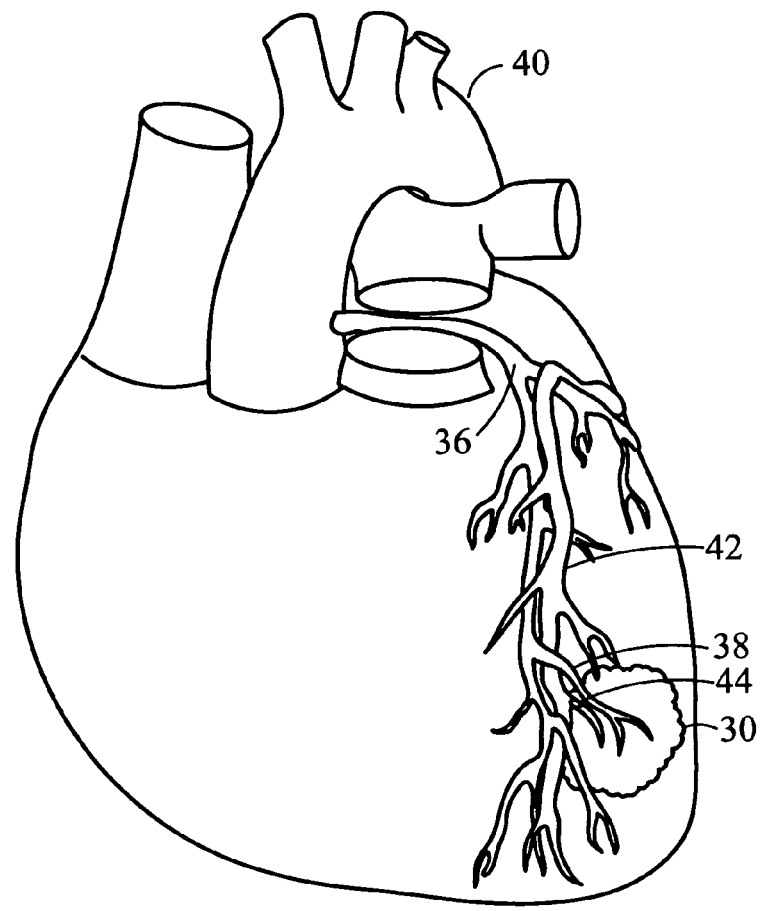
FIG. 3 is a schematic view of a heart with an infarct, showing vascular approaches to the infarct zone.
Figure 4:
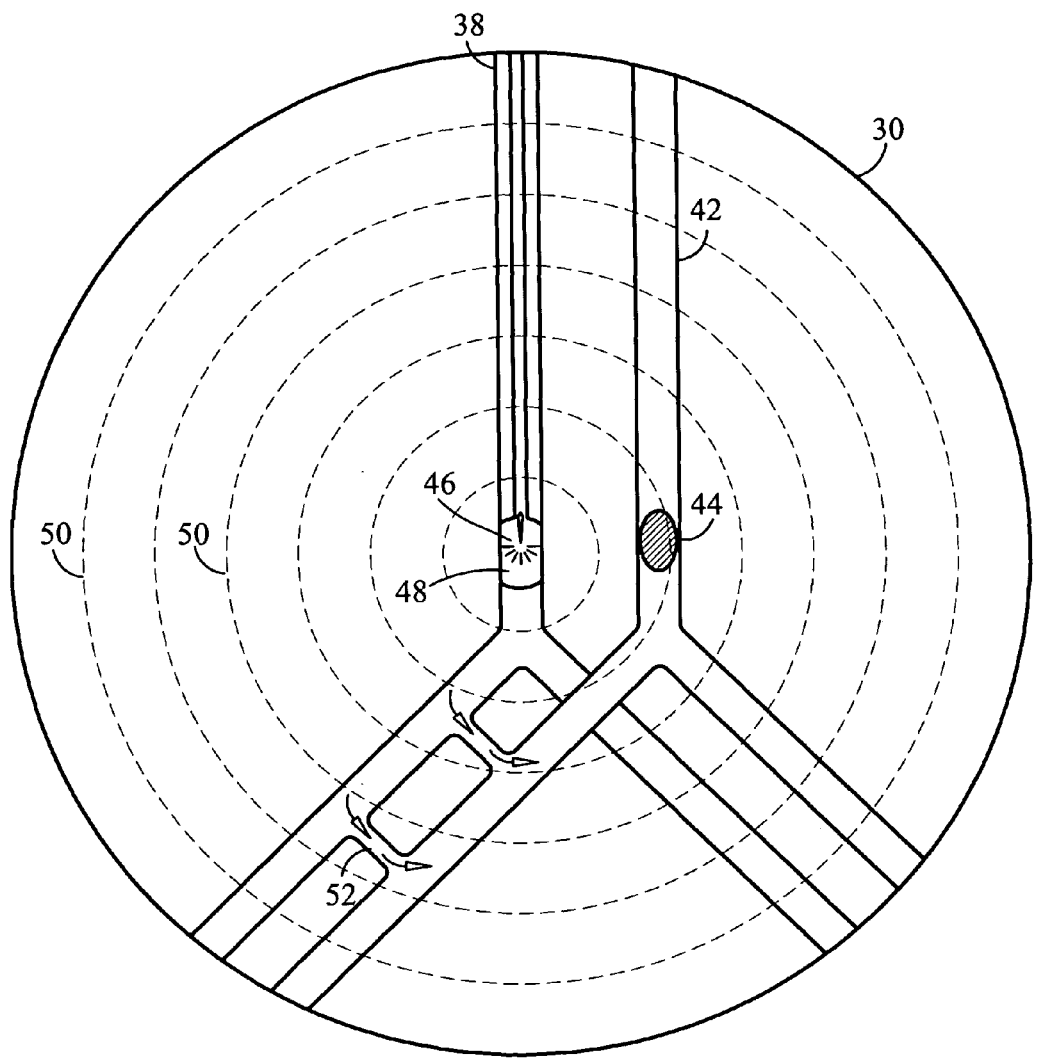
FIG. 4 is a more detailed view of the infarct zone of FIG. 3, illustrating placement of a cooling catheter in performance of a method in accordance with the invention
Figure 5:
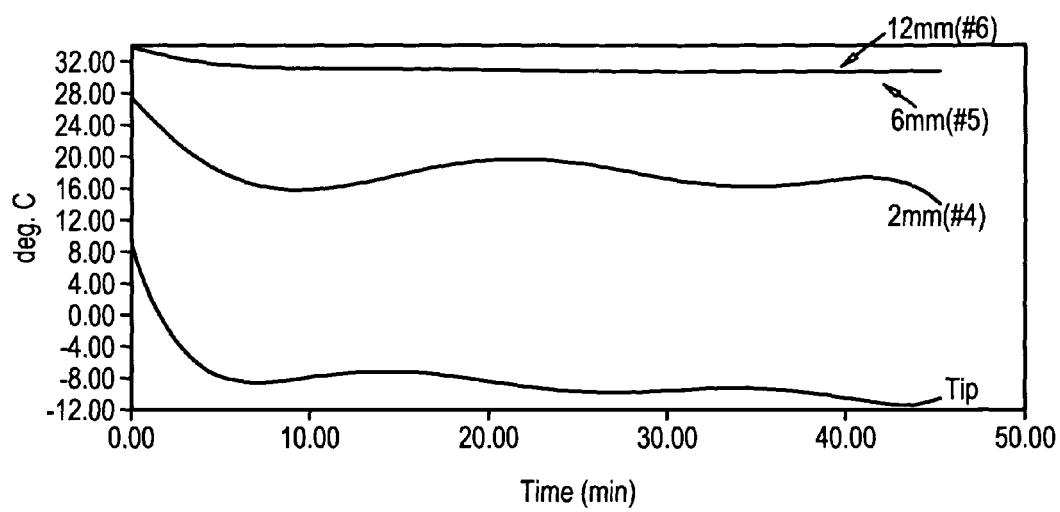
FIGS. 5-8 are graphs illustrating time versus temperature relationships at the cooling tip and tissue proximal the cooling tip.
Figure 6:
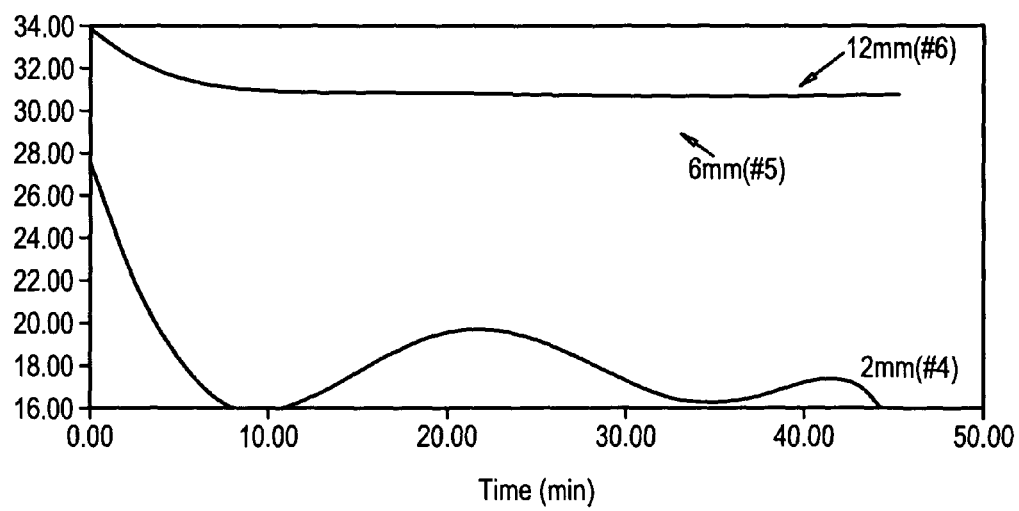
Figure 7:
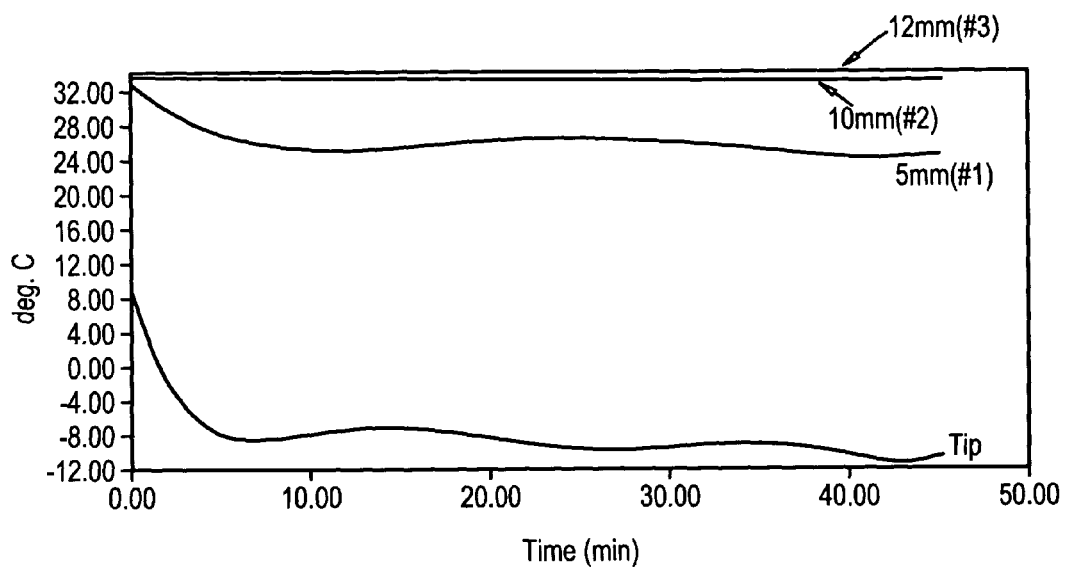
Figure 8:
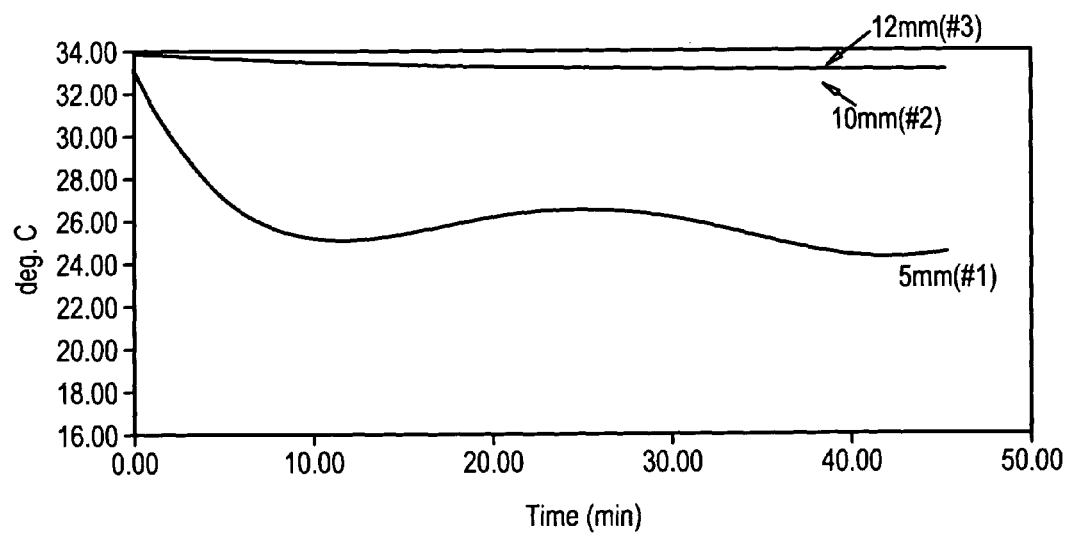

Referring now to FIGS. 2, 3 and 4, the method in accordance with the invention is shown with respect to a specific organ, namely, the heart. FIG. 2 is a cross-sectional illustration of a portion of a heart that has experienced a myocardial infarction 30. Surrounding the zone of the infarction 30 are zones of injury 32 and ischemia 34. It should be noted that although a portion of each zone is accessible from the exterior surface of the heart, that the greatest percentage of each zone extends well below the surface of the tissue and is not readily accessible from the surface. Depending upon the size of the zones, it can be extremely difficult, if not impossible, to cool all of the zones (or only the selected zones) to a predetermined temperature from the surface of the heart.

Thus, the method of the present invention advantageously provides for cooling of more than the surface of the zones, especially the subsurface regions, using a minimally invasive approach to the zones through the vasculature that leads to the zones. However, rather than merely cool the blood leading to the zones, the present invention provides for placement of a cooling structure or device, such as the working region of a highly flexible catheter within the zone adjacent the tissue to be treated, wherein the working region of the catheter is capable of thermal exchange with the tissue to cool the tissue to a predetermined temperature.

FIG. 3 is a schematic view of a heart with an infarct, showing vascular approaches for the device to the infarct zone 30. Cardiac structures of interest include a great cardiac vein 36, a distal cardiac vein 38, the aorta 40, a coronary distal artery 42, and an arterial blockage 44 within the coronary distal artery.

FIG. 4 is a more detailed view of the infarct zone 30 of FIG. 3. In this view the coronary distal artery 42 is shown with the arterial blockage 44. Also shown in the infarct zone 30 produced by the blockage is the distal cardiac vein 38.

A catheter 46 capable of tissue cooling is shown within the distal cardiac vein 38. As depicted, the catheter 46 can have a working region that includes a balloon or expandable tip 48. Alternatively, the working region 24 of the catheter 22 can be fixed diameter. The catheter 22 conducts a fluid (liquid, gas, or mixed liquid-gas) to and from the working region 24 as known in the art and as set forth in exemplary U.S. Pat. Nos. 5,899,899; 6,383,180; 6,635,053 and 6,648,880 that are assigned to CryoCath Technologies Inc, Montreal, Canada, all of which are incorporated herein by reference. In other embodiments, cooling can be provided by Pelletier or Piezoelectric devices.

When the catheter 46 is activated, the tissue immediately adjacent and proximate to the catheter is cooled. Generally, tissue temperature is coolest at a point closest to the working region 48. Exemplary temperature gradients 50 are shown in dashed lines as concentric regions. Significantly, only the zones of interest are cooled rather than the entire organ, thereby permitting the remainder of the organ to function normally.

Examples of such cooling isotherms are shown in FIGS. 5-8. The temperatures curves (each line represents a particular distance from the cooling catheter) are drawn at progressively large distances from the cooling catheter when the cooling catheter is placed in a normally perfused pig heart. It can be seen that cooling below 36 deg. C. can be achieved at up to 15 mm from the catheter surface resulting in a cooling cylinder volume of over 30 mm in diameter by the length of the cooling transfer zone of the catheter which can be up to approximately 100 mm. Even larger cooling zones may be achieved in ischemic tissue where heat loads are lower due to the lower blood flow.

Although not illustrated, additional apparatus used to place the catheter can include a guide sheath and wire. Alternatively, the catheter tip can be shaped (angled or curved approximately 45 degrees) or deflectable and the catheter shaft can have sufficient pushability and torqueability to be placed in the desired location without the aid of a guide wire or guide sheath/catheter. Further still, the catheter can be configured to allow blood to flow through a portion thereof after it has been placed and while it is cooling tissue.

Placement and activation of the catheter 46 can result in relatively instantaneous tissue cooling (within seconds rather than minutes or hours) to a temperature that is significantly below normal body temperature and potentially to temperatures approaching 0 degrees Centigrade near the working region 48, thereby protecting tissue, such as that immediately downstream of the arterial blockage 44. Thus, while the tissue is being protected from ischemic damage and reperfusion injury, other procedures can be implemented to remove the arterial blockage 44; and because the tissue is being protected, the window of time available to unblock the artery prior to irreversible organ damage is increased. Further, lowering the tissue temperature prior to reperfusion minimizes necrosis and salvages myocardium more than simply cooling the tissue to extend the window.

An exemplary implementation of the method in accordance with the invention is as follows for a patient diagnosed with an infarct due to embolic blockage. A central venous line may be placed, thrombolysis initiated and the patient transported to an interventional catheter lab/angiography suite or surgical suite. It should be noted, however, that Thrombolysis is the exception rather than the rule. In most cases the patient will be taken directly to the cath lab and the vessel reopened using interventional techniques (PTCA+/−stent). Thrombolysis will only be used when PTCA is not immediately available. Diagnostic tools such as an electrocardiogram (ECG) are used to confirm existence of an infarct and to determine its general location.

The patient's inguinal region is sterilely prepped and infiltrated with lidocaine. The femoral artery is accessed through an arterial puncture in the inguinal area and an introducer and guide wire are placed. An angiographic catheter is advanced and using standard contrast techniques and the specific location of stenosis or blockage is determined. However, this step may not be performed if the patient has received lytic therapy, and the ECG may be relied upon to determine infarct location.

Having located the treatment site, the catheter 46 is introduced into right atrium, through the coronary sinus and cardiac venous system to a venous location adjacent to the infarct-related artery, and/or in the approximate location of the infarct. The catheter 46 may have an ECG ring (not shown) to help specifically locate the infarct zone where the ECG signal is absent or weak. Cooling is initiated by flowing refrigerant through the working region 48 until a target temperature in the range of about 0 degrees C. to +34 degrees C. is reached. In this process, heat is absorbed from the tissue, cooling it to below 32 degrees C. Cooling of the infarct zone 30 can occur via two mechanisms: direct cooling of tissue within or adjacent to infarct; and direct cooling of blood which will retroperfuse through capillaries 52 to the infarct zone as illustrated in FIG. 4. Unlike existing systems, cooling will not occur through blood mixing flowing past the catheter tip since there will be no appreciable flow past the catheter 46. The catheter 46 may be left in place for up to 24 hours.

It will be appreciated by persons skilled in the art that the present invention is not limited to what has been particularly shown and described herein above. For example, although the above method has been described with respect to the heart, a similar approach can be taken with respect to any ischemic tissue of any organ. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for treating injured ischemic and infarcted tissue comprising:

positioning a first independent device within a vein of a target organ, wherein the first device has a cooling balloon capable of providing sufficient thermal exchange to cool adjacent tissue;

positioning a second independent device within an artery of the target organ, the artery having an endogenous arterial blockage therein, the second device being positioned proximate the arterial blockage and being capable of at least partially removing the arterial blockage from the artery, the first device being positioned within the vein of the target organ at a location proximate the arterial blockage;

activating the first device to cool adjacent tissue to a temperature in the range of 0 degrees Centigrade to +36 degrees Centigrade; and at least partially removing the arterial blockage from the artery using the second device.

2. The method of claim 1, wherein the first device is a catheter.

3. The method of claim 1, wherein the working region of the first device is a balloon element.

4. A method for treating injured ischemic and infarcted tissue comprising:

placing a first catheter-based device capable of passage through the venous system into a vein of a target organ proximate an arterial blockage within an artery of the target organ, wherein the first device is capable of providing sufficient thermal exchange at a working region thereof to cool adjacent tissue, wherein the working region of the first catheter-based device is a cooling balloon element;

activating the device to cool adjacent tissue to a temperature in the range of 0 degrees Centigrade to +36 degrees Centigrade; and placing a second catheter-based device capable of passage through the arterial system into an artery of the target organ proximate the location of the first catheter-based device, wherein the second catheter-based device is capable of at least partially removing the arterial blockage from the artery of the target organ.

5. The method of claim 4, wherein the arterial blockage is an endogenous arterial blockage.

6. The method of claim 5, wherein the endogenous arterial blockage is a blood clot.

* * * * *